United States Patent
Yoo

(10) Patent No.: US 11,093,038 B2
(45) Date of Patent: Aug. 17, 2021

(54) SYSTEMS AND METHODS FOR GENERIC CONTROL USING A NEURAL SIGNAL

(71) Applicant: Synchron Australia Pty Limited, Melbourne (AU)

(72) Inventor: Peter Eli Yoo, Fitzroy (AU)

(73) Assignee: Synchron Australia Pty Limited, Melbourne (AU)

( * ) Notice: Subject to any disclaimer, the term of this patent is extended or adjusted under 35 U.S.C. 154(b) by 0 days.

(21) Appl. No.: 16/457,493

(22) Filed: Jun. 28, 2019

(65) Prior Publication Data

US 2020/0363869 A1    Nov. 19, 2020

Related U.S. Application Data

(60) Provisional application No. 62/847,737, filed on May 14, 2019.

(51) Int. Cl.
*G06F 3/01* (2006.01)
*A61B 5/24* (2021.01)
*A61B 5/00* (2006.01)

(52) U.S. Cl.
CPC ............... *G06F 3/015* (2013.01); *A61B 5/24* (2021.01); *A61B 5/7267* (2013.01); *G06F 2203/011* (2013.01)

(58) Field of Classification Search
CPC ............. G06F 3/015; G06F 2203/011; A61B 5/04001–04009; A61B 5/24; A61B 5/293; A61B 5/316; A61B 5/374; A61B 5/375; A61B 5/6868; A61B 5/6862; A61B 5/7267; A61B 5/742; A61F 4/00
See application file for complete search history.

(56) References Cited

U.S. PATENT DOCUMENTS

| | | | |
|---|---|---|---|
| 9,445,739 B1 | 9/2016 | Payton et al. | |
| 2012/0296476 A1* | 11/2012 | Cale | G06F 3/015 700/276 |
| 2015/0338917 A1* | 11/2015 | Steiner | H04L 9/3231 345/156 |
| 2017/0281086 A1* | 10/2017 | Donaldson | A61B 5/14532 |
| 2019/0038438 A1* | 2/2019 | John | A61F 2/68 |
| 2019/0046119 A1 | 2/2019 | Oxley | |

FOREIGN PATENT DOCUMENTS

| | | |
|---|---|---|
| WO | WO 2006/078432 | 7/2006 |
| WO | WO 2010/121300 | 10/2010 |
| WO | WO 2014/102722 | 7/2014 |

* cited by examiner

*Primary Examiner* — Liliana Cerullo
(74) *Attorney, Agent, or Firm* — Levine Bagade Han LLP

(57) ABSTRACT

Universal switch modules, universal switches, and methods of using the same are disclosed, including methods of preparing an individual to interface with an electronic device or software. For example, a method is disclosed that can include measuring brain-related signals of the individual to obtain a first sensed brain-related signal when the individual generates a task-irrelevant thought. The method can include transmitting the first sensed brain-related signal to a processing unit. The method can include associating the task-irrelevant thought and the first sensed brain-related signal with N input commands. The method can include compiling the task-irrelevant thought, the first sensed brain-related signal, and the N input commands to an electronic database.

17 Claims, 6 Drawing Sheets

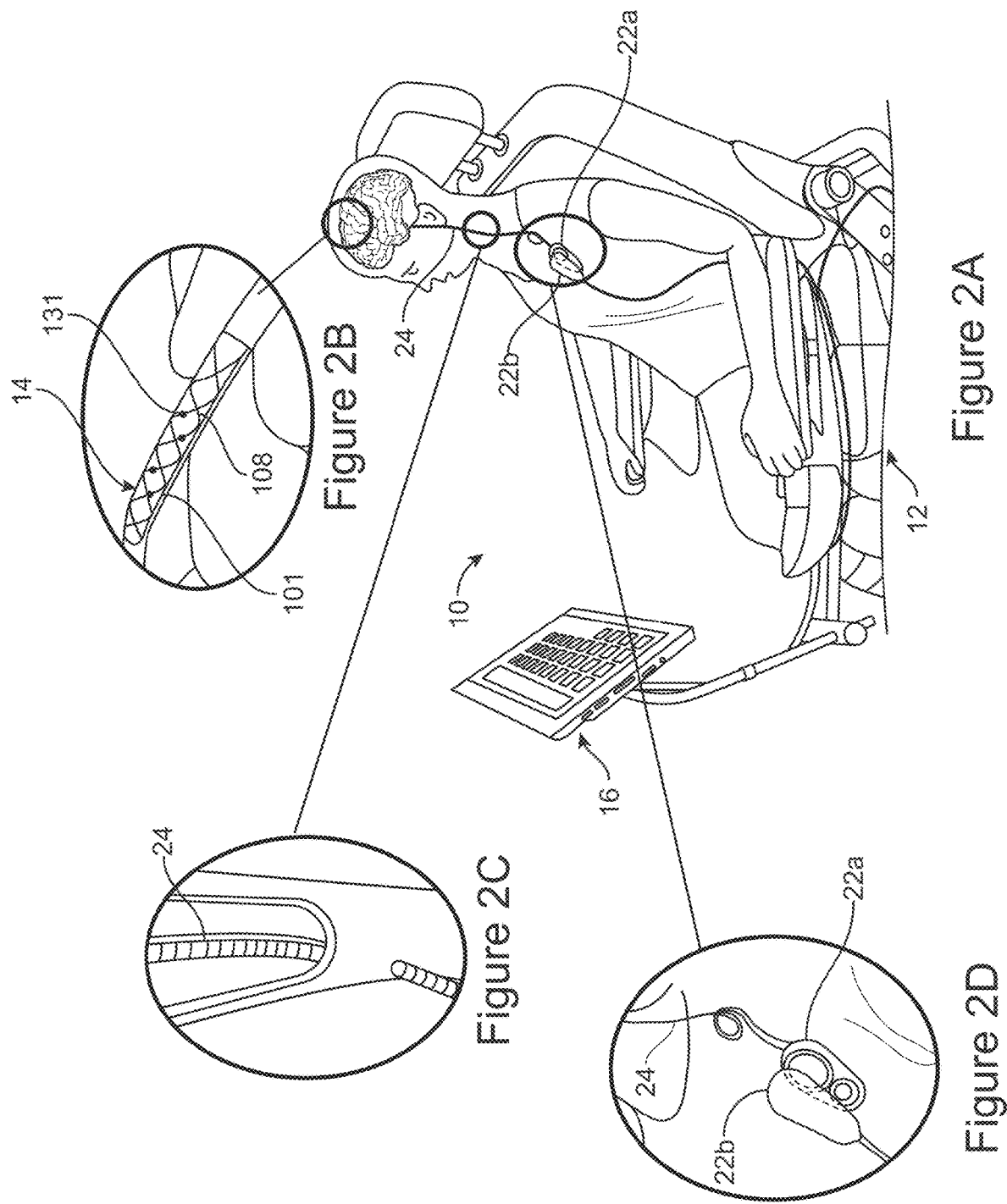

US 11,093,038 B2

SYSTEMS AND METHODS FOR GENERIC CONTROL USING A NEURAL SIGNAL

CROSS-REFERENCE TO RELATED APPLICATIONS

This application claims priority to U.S. Provisional Application No. 62/847,737 filed May 14, 2019, which is herein incorporated by reference in its entirety for all purposes.

BACKGROUND

1. Technical Field

This disclosure relates generally to methods of using neural-related signals and more particularly to methods of using neural signals as universal switches.

2. Background of the Art

Currently for brain computer interfaces (BCIs), users are asked to either perform a task-relevant mental task to perform a given target task (e.g., try moving a cursor when the target task is to move a cursor) or are asked to perform a task-irrelevant mental task to perform a given target task (e.g., try moving your hand to move a cursor to the right). Furthermore, current BCIs only allow users to use the thought (e.g., the task-relevant mental task or the task-irrelevant mental task) to control a pre-defined target task that is set by the researcher. This disclosure describes novel methods and systems that prepare and allow BCI users to utilize a given task-irrelevant thought to independently control a variety of end-applications, including software and devices.

BRIEF SUMMARY OF THE INVENTION

Systems and methods of control using neural-related signals are disclosed, including universal switches and methods of using the same.

Methods of preparing an individual to interface with an electronic device or software are disclosed. For example, a method is disclosed that can include measuring neural-related signals of the individual to obtain a first sensed neural signal when the individual generates a first task-irrelevant thought. The method can include transmitting the first sensed neural signal to a processing unit. The method can include associating the first task-irrelevant thought and the first sensed neural signal with a first input command. The method can include compiling the first task-irrelevant thought, the first sensed neural signal, and the first input command to an electronic database.

Methods of controlling a first device and a second device are disclosed. For example, a method is disclosed that can include measuring neural-related signals of an individual to obtain a sensed neural signal when the individual generates a task-irrelevant thought. The method can include transmitting the sensed neural signal to a processor. The method can include associating, via the processor, the sensed neural signal with a first device input command and a second device input command. The method can include upon associating the sensed neural signal with the first device input command and the second device input command, electrically transmitting the first device input command to the first device or electrically transmitting the second device input command to the second device.

Methods of preparing an individual to interface with a first device and a second device are disclosed. For example, a method is disclosed that can include measuring a brain-related signal of the individual to obtain a sensed brain-related signal when the individual generates a task-specific thought by thinking of a first task. The method can include transmitting the sensed brain-related signal to a processing unit. The method can include associating, via the processing unit, the sensed brain-related signal with a first device input command associated with a first device task. The first device task is different from the first task. The method can include associating, via the processing unit, the sensed brain-related signal with a second device input command associated with a second device task. The second device task is different from the first device task and the first task. The method can include upon associating the sensed brain-related signal with the first device input command and the second device input command, electrically transmitting the first device input command to the first device to execute the first device task associated with the first device input command or electrically transmitting the second device input command to the second device to execute the second device task associated with the second device input command.

BRIEF SUMMARY OF THE DRAWINGS

The drawings shown and described are exemplary embodiments and non-limiting. Like reference numerals indicate identical or functionally equivalent features throughout.

FIGS. 2A-2D illustrate a variation of a universal switch model in communication with an end application.

DETAILED DESCRIPTION

Figure 1A:
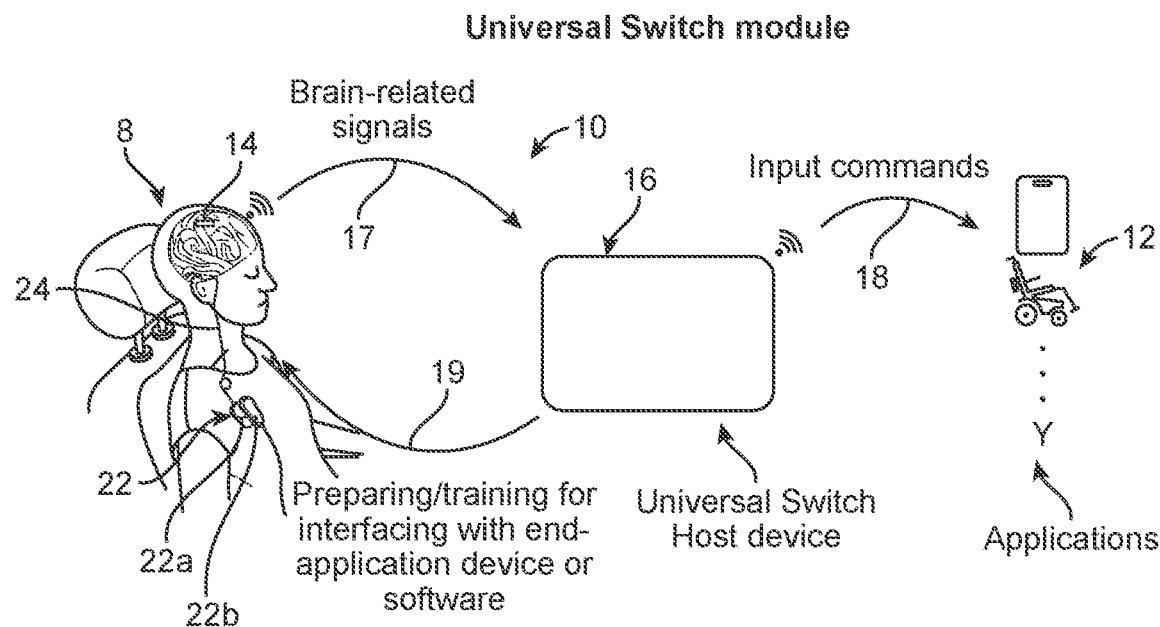
FIG. 1A illustrates a variation of a universal switch module.
Figure 1B:
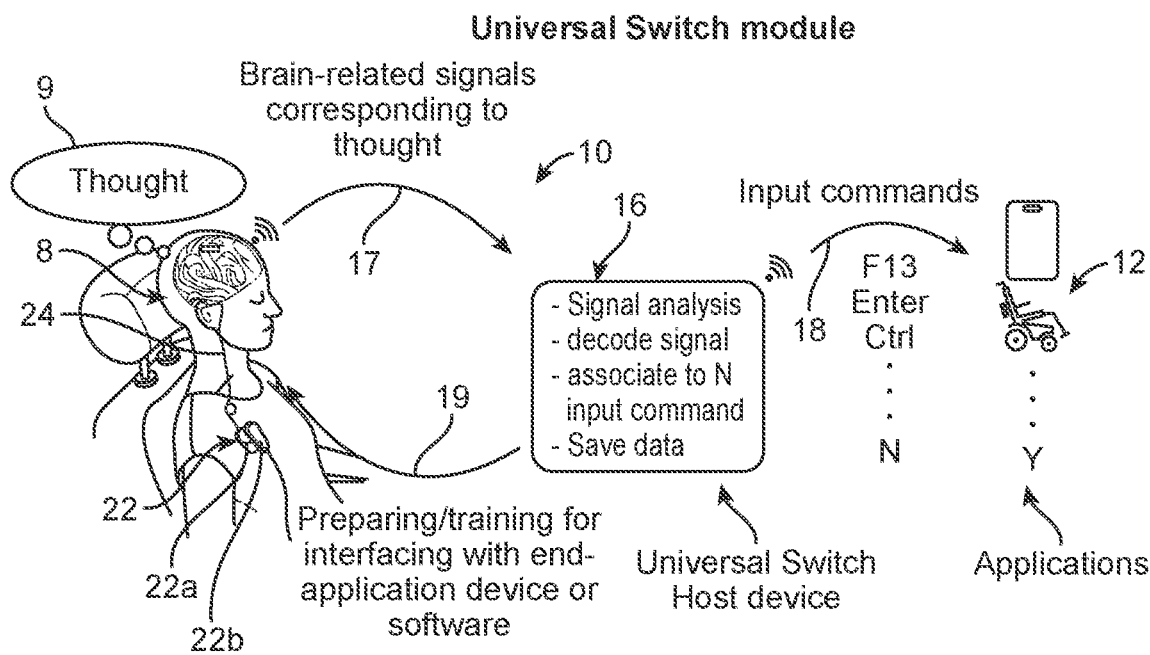
FIG. 1B illustrates a variation of the universal switch module of FIG. 1A when the patient is thinking of a thought.
Figure 1C:
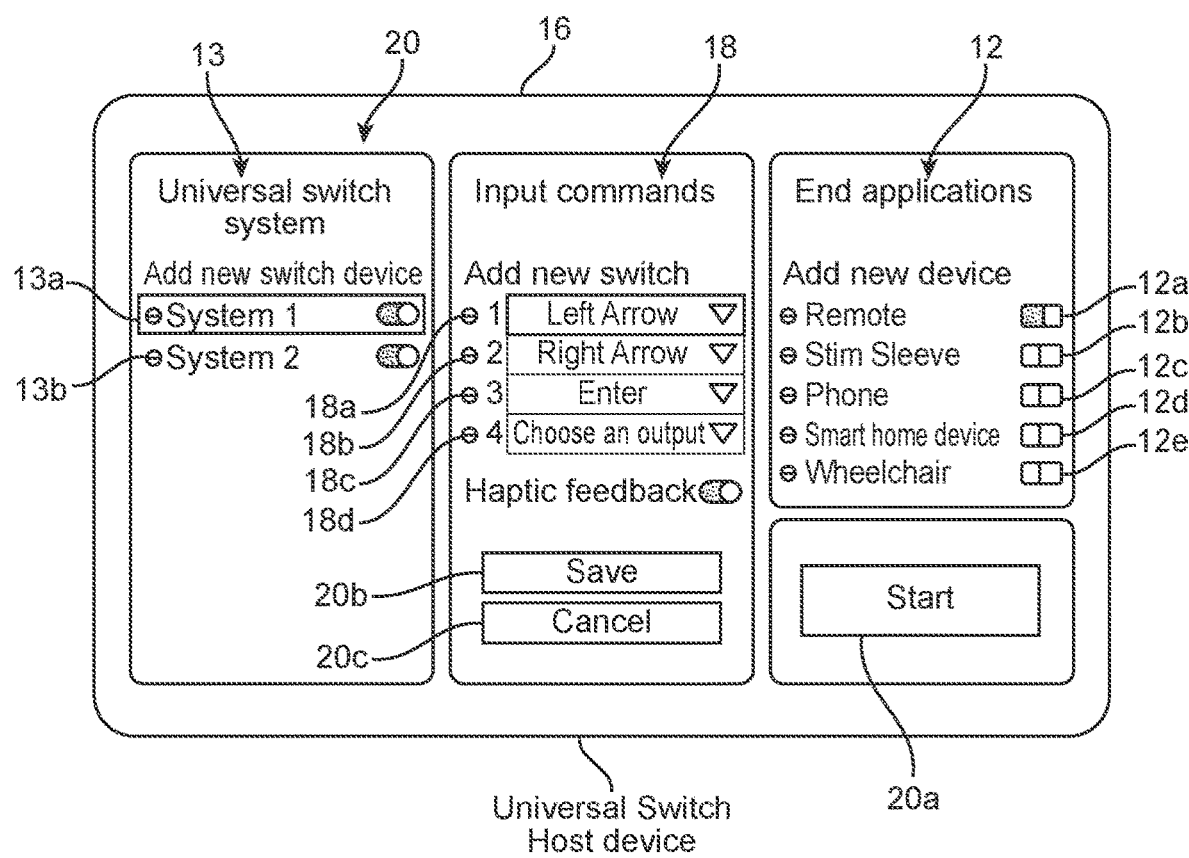
FIG. 1C illustrates a variation of a user interface of a host device of the universal switch module of FIGS. 1A and 1B.

Universal switch modules, universal switches, and methods of using the same are disclosed. For example, FIGS. 1A-1C illustrate a variation of a universal switch module 10 that a patient 8 (e.g., BCI user) can use to control one or multiple end applications 12 by thinking of a thought 9. The module 10 can include a neural interface 14 and a host device 16. The module 10 (e.g., the host device 16) can be in wired and/or wireless communication with the one or multiple end applications 12. The neural interface 14 can be a biological medium signal detector (e.g., an electrical conductor, a biochemical sensor), the host device 16 can be a computer (e.g., laptop, smartphone), and the end applications 12 can be any electronic device or software. The neural interface 14 can, via one or multiple sensors, monitor the neural-related signals 17 of the biological medium. A processor of the module 10 can analyze the detected neural-related signals 17 to determine whether the detected neural-related signals 17 are associated with a thought 9 assigned to an input command 18 of an end application 12. When a thought 9 that is assigned to an input command 18 is detected by the neural interface 14 and associated with the input command 18 by the processor, the input command 18 can be sent (e.g., via the processor, a controller, or a transceiver) to the end application 12 that that input command 18 is associated with. The thought 9 can be assigned to input of commands 18 of multiple end applications 12. The module 10 thereby advantageously enables the patient 8 to independently control multiple end applications 12 with a single thought (e.g., the thought 9), for example, a first end application and a second end application, where the thought 9 can be used to control the first and second applications at different times and/or at the same time. In this way, the module 10 can function as a universal switch module, capable of using the same thought 9 to control multiple end applications 12 (e.g., software and devices). The thought 9 can be a universal switch, assignable to any input command 18 of any end application 12 (e.g., to an input command 18 of the first end application and to an input command 18 of the second end application). The first end application can be a first device or first software. The second end application can be a second device or second software.

When the patient 8 thinks of the thought 9, the input commands 18 that are associated with the thought 9 can be sent to their corresponding end applications 12 by the module 10 (e.g., via a processor, a controller, or a transceiver). For example, if the thought 9 is assigned to an input command 18 of the first end application, the input command 18 of the first end application can be sent to the first end application when the patient 8 thinks of the thought 9, and if the thought 9 is assigned to an input command 18 of the second end application, the input command 18 of the second end application can be sent to the second end application when the patient 8 thinks of the thought 9. The thought 9 can thereby interface with, or control, multiple end applications 12, such that the thought 9 can function like a universal button (e.g., the thought 9) on a universal controller (e.g., the patient's brain). Any number of thoughts 9 can be used as switches. The number of thoughts 9 used as switches can correspond to, for example, the number of controls (e.g., input commands 18) needed or desired to control an end application 12.

To use video game controllers as an example, the patient's thoughts 9 can be assigned to any input command 18 associated with any individual button, any button combination, and any directional movement (e.g., of a joystick, of a control pad such as a directional pad) of the controller, such that that the patient 8 can play any game of any video game system using their thoughts 9 with or without the presence of a conventional physical controller. Video game systems are just one example of end applications 12. The module 10 enables the thoughts 9 to be assigned to the input commands 18 of any end application 12 such that the patient's thoughts 9 can be mapped to the controls of any software or device. The module 10 can thereby organize the patient's thoughts 9 into a group of assignable switches, universal in nature, but specific in execution once assigned to an input command 18. Additional exemplary examples of end applications 12 include mobility devices (e.g., vehicles, wheelchairs, wheelchair lifts), prosthetic limbs (e.g., prosthetic arms, prosthetic legs), phones (e.g., smartphones), smart household appliances, and smart household systems.

The neural interface 14 can detect neural-related signals 17, including those associated with the thoughts 9 and those not associated with the thoughts 9. For example, the neural interface 14 can have one or multiple sensors that can detect (also referred to as obtain, sense, record, and measure) the neural-related signals 17, including those that are generated by a biological medium of the patient 8 when the patient 8 thinks of a thought 9, and including those that are generated by a biological medium of the patient 8 not associated with the thought 9 (e.g., form the patient responding to stimuli not associated with the thought 9). The sensors of the neural interface 14 can record signals from and/or stimulate a biological medium of the patient 8. The biological medium can be, for example, neural tissue, vascular tissue, blood, bone, muscle, cerebrospinal fluid, or any combination thereof. The sensors can be, for example, electrodes, where an electrode can be any electrical conductor for sensing electrical activity of the biological medium. The sensors can be, for example, biochemical sensors. The neural interface 14 can have a single type of sensor (e.g., only electrodes) or multiple types of sensors (e.g., one or multiple electrodes and one or multiple biochemical sensors).

The neural-related signals can be any signal (e.g., electrical, biochemical) detectable from the biological medium, can be any feature or features extracted from a detected neural-related signal (e.g., via a computer processor), or both, where extracted features can be or can include characteristic information about the thoughts 9 of the patient 8 so that different thoughts 9 can be distinguished from one another. As another example, the neural-related signals can be electrical signals, can be any signal (e.g., biochemical signal) caused by an electrical signal, can be any feature or features extracted from a detected neural-related signal (e.g., via a computer processor), or any combination thereof. The neural-related signals can be neural signals such as brainwaves. Where the biological medium is inside the patient's skull, the neural-related signals can be, for example, brain signals (e.g., detected from brain tissue) that result from or are caused by the patient 8 thinking of the thought 9. In this way, the neural-related signals can be brain-related signals such as electrical signals from any portion or portions of the patient's brain (e.g., motor cortex, sensory cortex). Where the biological medium is outside the patient's skull, the neural-related signals can be, for example, electrical signals associated with muscle contraction (e.g., of a body part such as an eyelid, an eye, the nose, an ear, a finger, an arm, a toe, a leg) that result from or are caused by the patient 8 thinking of the thought 9. The thoughts 9 (e.g., movement of a body part, a memory, a task) that the patient 8 thinks of when neural-related signals are being detected from their brain tissue can be the same or different than the thoughts 9 that the patient 8 thinks of when neural-related signals are being detected from non-brain tissue. The neural interface 14 can be positionable inside the patient's brain, outside the patient's brain, or both.

The module 10 can include one or multiple neural interfaces 14, for example, 1 to 10 or more neural interfaces 14, including every 1 neural interface increment within this range (e.g., 1 neural interface, 2 neural interfaces, 10 neural interfaces), where each neural interface 14 can have one or multiple sensors (e.g., electrodes) configured to detect neural-related signals (e.g., neural signals). The location of the neural interfaces 14 can be chosen to optimize the recording of the neural-related signals, for example, such as selecting the location where the signal is strongest, where interference from noise is minimized, where trauma to the patient 8 caused by implantation or engagement of the neural interface 14 to the patient 8 (e.g., via surgery) is minimized, or any combination thereof. For example, the neural interface 14 can be a brain machine interface such as an endovascular device (e.g., a stent) that has one or multiple electrodes for detecting electrical activity of the brain. Where multiple neural interfaces 14 are used, the neural interfaces 14 can be the same or different from one another. For example, where two neural interfaces 14 are used, both of the neural interfaces 14 can be an endovascular device having electrodes (e.g., an expandable and collapsible stent having electrodes), or one of the neural interfaces 14 can be an endovascular device having electrodes and the other of the two neural interfaces 14 can be a device having sensors that is different from an endovascular device having electrodes.

FIGS. 1A and 1B further illustrate that the module 10 can include a telemetry unit 22 adapted for communication with the neural interface 14 and a communication conduit 24 (e.g., a wire) for facilitating communications between the neural interface 14 and the telemetry unit 22. The host device 16 can be adapted for wired and/or wireless communication with the telemetry unit 22. The host device 16 can be in wired and/or wireless communication with the telemetry unit 22.

FIGS. 1A and 1B further illustrate that the telemetry unit 22 can include an internal telemetry unit 22a and an external telemetry unit 22b. The internal telemetry unit 22a can be in wired or wireless communication with the external telemetry unit 22b. For example, the external telemetry unit 22b can be wirelessly connected to the internal telemetry unit 22a across the patient's skin. The internal telemetry unit 22a can be in wireless or wired communication with the neural interface 14, and the neural interface 14 can be electrically connected to the internal telemetry unit 22a via the communication conduit 24. The communication conduit 24 can be, for example, a wire such as a stent lead.

The module 10 can have a processor (also referred to as a processing unit) that can analyze and decode the neural-related signals detected by the neural interface 14. The processor can be a computer processor (e.g., microprocessor). The processor can apply a mathematical algorithm or model to detect the neural-related signals corresponding to when the patient 8 generates the thought 9. For example, once a neural-related signal 17 is sensed by the neural interface 14, the processor can apply a mathematical algorithm or a mathematical model to detect, decode, and/or classify the sensed neural-related signal 17. As another example, once a neural-related signal 17 is sensed by the neural interface 14, the processor can apply a mathematical algorithm or a mathematical model to detect, decode, and/or classify the information in the sensed neural-related signal 17. Once the neural-related signal 17 detected by the neural interface 14 is processed by the processor, the processor can associate the processed information (e.g., the detected, decoded, and/or classified neural related signal 17 and/or the detected, decoded, and/or classified information of the sensed neural-related signal 17) to the input commands 18 of the end applications 12.

The neural interface 14, the host device 16, and/or the telemetry unit 22 can have the processor. As another example, the neural interface 14, the host device 16, and/or the telemetry unit 22 can have a processor (e.g., such as the processor described above). For example, the host device 16 can, via the processor, analyze and decode the neural-related signals 17 that are detected by the neural interface 14. The neural interface 14 can be in wired or wireless communication with the host device 16, and the host device 16 can be in wired or wireless communication with the end applications 12. As another example, the neural interface 14 can be in wired or wireless communication with the telemetry unit 22, the telemetry unit 22 can be in wired or wireless communication with the host device 16, and the host device 16 can be in wired or wireless communication with the end applications 12. Data can be passed from the neutral interface 14 to the telemetry unit 22, from the telemetry unit 22 to the host device 16, from the host device 16 to one or multiple end applications 12, or any combination thereof, for example, to detect a thought 9 and trigger an input command 18. As another example, data can be passed in the reverse order, for example, from one or multiple end applications 12 to the host device 16, from the host device 16 to the telemetry unit 22, from the telemetry unit 22 to the neural interface 14, or any combination thereof, for example, to stimulate the biological medium via one or more of the sensors. The data can be data collected or processed by the processor, including, for example, the neural-related signals and/or features extracted therefrom. Where data is flowing toward the sensors, for example, from the processor, the data can include stimulant instructions such that when the stimulant instructions are be processed by the neural interface 14, the sensors of the neural interface can stimulate the biological medium.

FIGS. 1A and 1B further illustrate that when the patient 8 thinks of a thought 9, a biological medium of the patient 8 (e.g., biological medium inside the skull, outside the skull, or both) can generate neural-related signals 17 that are detectable by the neural interface 14. The sensors of the neural interface 14 can detect the neural-related signals 17 associated with the thought 9 when the patient 8 thinks of the thought 9. The neural-related signals 17 associated with the thought 9, features extracted from these neural-related signals 17, or both can be assigned or associated with any input command 18 for any of the end applications 12 controllable with the universal switch module 10. Each of the detectable neural-related signals 17 and/or their extracted features can thereby advantageously function as a universal switch, assignable to any input command 18 for any end application 12. In this way, when a thought 9 is detected by the neural interface 14, the input command 18 associated with that thought 9 can be triggered and sent to the end application 12 that the triggered input command 18 is associated with.

For example, when a thought 9 is detected by the neural interface 14 (e.g., by way of a sensed neural-related signal 17), a processor can analyze (e.g., detect, decode, classify, or any combination thereof) the sensed neural-related signal 17 and associate the sensed neural-related signal 17 and/or features extracted therefrom with the corresponding assigned input commands 18. The processor can thereby determine whether or not the thought 9 (e.g., the sensed neural related signal 17 and/or features extracted therefrom) is associated with any of the input commands 18. Upon a determination that the thought 9 is associated with an input command 18, the processor or a controller can activate (also referred to as trigger) the input command 18. Once an input command 18 is triggered by the module 10 (e.g., by the processor or the controller of the host device 16), the triggered input command 18 can be sent to its corresponding end application 12 so that that end application 12 (e.g., wheelchair, prosthetic arm, smart household appliance such as a coffee machine) can be controlled with the triggered input command 18. Once the end application 12 receives the triggered input command 18, the end application 12 can execute the instruction or instructions of the input command 18 (e.g., move the wheel chair forward at 1 meter per second, pinch the thumb and index finger of the prosthetic arm together, turn on the smart coffee machine). Thus, upon a determination that a thought 9 (e.g., a sensed neural-related signal 17 and/or features extracted therefrom) is associated with an input command 18, the input command 18 can be sent to its corresponding end application 12.

The extracted features can be the components of the sensed neural-related signals 17, including, for example, patterns of voltage fluctuations in the sensed neural-related signals 17, fluctuations in power in a specific band of frequencies embedded within the sensed neural-related signals 17, or both. For example, the neural-related signals 17 can have a various range of oscillating frequencies that correspond with when the patient 8 thinks the thought 9. Specific bands of frequencies can contain specific information. For example, the high-band frequency (e.g., 65 Hz-150 Hz) can contain information that correlate with motor related thoughts, hence, features in this high-band frequency range can be used (e.g., extracted from or identified in the sensed neural-related signals 17) to classify and/or decode neural events (e.g., the thoughts 9).

The thought 9 can be a universal switch. The thought 9 can function (e.g., be used as) as a universal switch, where the thought 9 can be assigned to any input command 18, or vice versa. The thought 9—by way of the detectable neural-related signals 17 associated therewith and/or the features extractable therefrom—can be assigned or associated with any input command 18 for any of the end applications 12 controllable with the universal switch module 10. The patient 8 can activate a desired input command 18 by thinking of the thought 9 that is associated with the input command 18 that the patient 8 desires. For example, when a thought 9 (e.g., memory of the patient's 9th birthday party) that is assigned to a particular input command 18 (e.g., move a wheelchair forward) is detected by the neural interface 14, the processor (e.g., of the host device 16) can associate the neural-related signal 17 associated with that thought 9 (e.g., memory of 9th birthday party) and/or features extracted therefrom to the corresponding assigned input command 18 (e.g., move a wheelchair forward). When the detected neural-related signal (e.g., and/or extracted features associated therewith) are associated with an assigned input command 18, the host device 16 can, via the processor or a controller, send that input command 18 to the end application 12 that the input command 18 is associated with to control the end application 12 with the input command 18 that the patient 8 triggered by thinking of the thought 9.

Where the thought 9 is assigned to multiple end applications 12 and only one of the end applications 12 is active (e.g., powered on and/or running), the host device 16 can send the triggered input command 18 to the active end application 12. As another example, where the thought 9 is assigned to multiple end applications 12 and some of the end applications 12 are active (e.g., powered on or running) and some of the end applications 12 are inactive (e.g., powered off or in standby mode), the host device 16 can send the triggered input command 18 to both the active and inactive end applications 12. The active end applications 12 can execute the input command 18 when the input command 18 is received by the active end applications 12. The inactive end applications 12 can execute the input command 18 when the inactive applications 12 become active (e.g., are powered on or start running), or the input command 18 can be placed in a queue (e.g., by the module 16 or by the end application 12) to be executed when the inactive applications 12 become active. As yet another example, where the thought 9 is assigned to multiple end applications 12 and more than one of the end applications 12 is active (e.g., powered on and/or running), for example, a first end application and a second end application, the host device 16 can send the triggered input command 18 associated with the first end application to the first end application and can send the triggered input command 18 associated with the second end application to the second end application, or the module 10 can give the patient 8 a choice of which of the triggered input commands 18 the patient 8 would like to send (e.g., send only the triggered input command 18 associated with the first end application, send only the triggered input command 18 associated with the second end application, or send both of the triggered input commands 18).

The thought 9 can be any thought or combination of thoughts. For example, the thought 9 that the patient 8 thinks of can be a single thought, multiple thoughts, multiple thoughts in series, multiple thoughts simultaneously, thoughts having different durations, thoughts having different frequencies, thoughts in one or multiple orders, thoughts in one or multiple combinations, or any combination thereof. A thought 9 can be a task-relevant thought, a task-irrelevant thought, or both, where task-relevant thoughts are related to the intended task of the patient 8 and where the task-irrelevant thoughts are not related to the intended task of the patient 8. For example, the thought 9 can be of a first task and the patient 8 can think of the first task to complete a second task (also referred to as the intended task and target task), for example, by using the module 10. The first task can be the same or different from the second task. Where the first task is the same as the second task, the thought 9 can be a task-relevant thought. Where the first task is different from the second task, the thought 9 can be a task-irrelevant thought. For example, where the first task that the patient 8 thinks of is moving a body limb (e.g., arm, leg) and the second task is the same as the first task, namely, moving a body limb (e.g., arm, leg), for example, of a prosthetic body limb, the thought 9 (e.g., of the first task) can be a task-relevant thought. The prosthetic body limb can be, for example, the end application 12 that the patient 8 is controlling with the thought 9. For example, for a task-relevant thought, the patient 8 can think of moving a cursor when the target task is to move a cursor. In contrast, for a task-irrelevant thought 9, where the patient 8 thinks of moving a body limb (e.g., arm) as the first task, the second task can be any task different from the first task of moving a body limb (e.g., arm) such that the second task can be a task of any end application 12 that is different from the first task. For example, for a task-irrelevant thought, the patient 8 can think of moving a body part (e.g., their hand) to the right when the target task is to move a cursor to the right. The patient 8 can thereby think of the first task (e.g., thought 9) to accomplish any second task, where the second task can be the same or different from the first task. The second task can be any task of any end application 12. For example, the second task can be any input command 18 of any end application 12. The thought 9 (e.g., the first task) can be assignable to any second task. The thought 9 (e.g., the first task) can be assigned to any second task. The patient 8 can thereby think of the first task to trigger any input command 18 (e.g., any second task) of any end application 12. The first task can thereby advantageously function as a universal switch. Each thought 9 can produce a repeatable neural-related signal detectable by the neural interface 14 (e.g., the detectable neural-related signals 17). Each detectable neural-related signal and/or features extractable therefrom can be a switch. The switch can be activated (also referred to as triggered), for example, when the patient 8 thinks of the thought 9 and the sensor detects that the switch is activated and/or the processor determines that one or multiple extracted features from the detected neural-related signal are present. The switch can be a universal switch, assignable and re-assignable to any input command 18, for example, to any set of input commands. Input commands 18 can be added to, removed from, and/or modified from any set of input commands. For example, each end application 12 can have a set of input commands 18 associated therewith to which the neural-related signals 17 of the thoughts 9 can be assigned to.

Some of the thoughts 9 can be task-irrelevant thoughts (e.g., the patient 8 tries moving their hand to move a cursor to the right), some of the thoughts 9 can be task-relevant thoughts (e.g., the patient 8 tries moving a cursor when the target task is to move a cursor), some of the thoughts 9 can be both a task-irrelevant thought and a task-relevant thought, or any combination thereof. Where a thought 9 is both a task-irrelevant thought and a task-relevant thought, the thought 9 can be used as both a both a task-irrelevant thought (e.g., the patient 8 tries moving their hand to move a cursor to the right) and a task-relevant thought (e.g., the patient tries moving a cursor when the target task is to move a cursor) such that the thought 9 can be associated with multiple input commands 18, where one or multiple of those input commands 18 can be task-relevant to the thought 9 and where one or multiple of those input commands 18 can be task-irrelevant to the thought 9.

In this way, the thought 9 can be a universal switch assignable to any input command 18 for any end application 12, where each thought 9 can be assigned to one or multiple end applications 12. The module 10 advantageously enables each patient 8 to use their thoughts 9 like buttons on a controller (e.g., video game controller, any control interface) to control any end application 12 that the patient 8 would like. For example, a thought 9 can be assigned to each input command 18 of an end application 12, and the assigned input commands 18 can be used in any combination, like buttons on a controller, to control the end application 12. For example, where an end application 12 has four input commands 18 (e.g., like four buttons on a controller—a first input command, a second input command, a third input command, and a fourth input command), a different thought 9 can be assigned to each of the four input commands 18 (e.g., a first thought 9 can be assigned to the first input command 18, a second thought 9 can be assigned to the second input command 18, a third thought 9 can be assigned to the third input command 18, and a fourth thought 9 can be assigned to the fourth input command 18) such that the patient 8 can use these four thoughts 9 to activate the four input commands 18 and combinations thereof (e.g., any order, number, frequency, and duration of the four input commands 18) to control the end application 12. For example, for an end application 12 having four input commands 18, the four input commands 18 can be used to control the end application 12 using any combination of the four thoughts 9 assigned to the first, second, third, and fourth input commands 18, including, for example, a single activation of each input command by itself, multiple activations of each input command by itself (e.g., two activations in less than 5 second, three activations in less than 10 seconds), a combination of multiple input commands 18 (e.g., the first and second input command simultaneously or in series), or in any combination thereof. Like each individual thought 9, each combination of thoughts 9 can function as a universal switch. The patient 8 can control multiple end applications 12 with the first, second, third, and fourth thoughts 9. For example, the first thought 9 can be assigned to a first input command 18 of a first end application 12, the first thought 9 can be assigned to a first input command 18 of a second end application 12, the second thought 9 can be assigned to a second input command 18 of the first end application 12, the second thought 9 can be assigned to a second input command 18 of the second end application 12, the third thought 9 can be assigned to a third input command 18 of the first end application 12, the third thought 9 can be assigned to a third input command 18 of the second end application 12, the fourth thought 9 can be assigned to a fourth input command 18 of the first end application 12, the fourth thought 9 can be assigned to a fourth input command 18 of the second end application 12, or any combination thereof. For example, the first thought 9 can be assigned to a first input command 18 of a first end application 12 and to a first input command 18 of a second end application 12, the second thought 9 can be assigned to a second input command 18 of the first end application 12 and to a second input command 18 of the second end application 12, the third thought 9 can be assigned to a third input command 18 of the first end application 12 and to a third input command 18 of the second end application 12, the fourth thought 9 can be assigned to a fourth input command 18 of the first end application 12 and to a fourth input command 18 of the second end application 12, or any combination thereof. The first, second, third, and fourth thoughts 9 can be assigned to any application 12 (e.g., to first and second end applications). Some thoughts may only be assigned to single application 12 and some thoughts may be assigned to multiple applications 12. Even where a thought 9 is only assigned to a single application 12, the thought that is only assigned to one application 12 can be assignable to multiple applications 12 such that the patient 8 can take advantage of the universal applicability of the thought 9 (e.g., that is assigned to only one end application 12) on an as needed or as desired basis. As another example, all thoughts 9 may be assigned to multiple end applications 12.

The function of each input command 18 or combination of input commands for an end application 12 can be defined by the patient 8. As another example, the function of each input command 18 or combination of input commands for an end application 12 can be defined by the end application 12, such that third parties can plug into and have their end application input commands 18 assignable (also referred to as mapable) to a patient's set or subset of repeatable thoughts 9. This can advantageously allow third party programs to be more accessible to and tailor to the differing desires, needs, and capabilities of different patients 8. The module 10 can advantageously be an application programming interface (API) that third parties can interface with and which allows the thoughts 9 of patients 8 to be assigned and reassigned to various input commands 18, where, as described herein, each input command 18 can be activated by the patient 8 thinking of the thought 9 that is assigned to the input command 18 that the patient 8 wants to activate.

A patient's thoughts 9 can be assigned to the input commands 18 of an end application 12 via a person (e.g., the patient or someone else), a computer, or both. For example, the thoughts 9 of the patient 8 (e.g., the detectable neural-related signals and/or extractable features associated with the thoughts 9) can assigned the input commands 18 by the patient 8, can be assigned by a computer algorithm (e.g., based on signal strength of the detectable neural-related signal associated with the thought 9), can be changed (e.g., reassigned) by the patient 8, can be changed by an algorithm (e.g., based on relative signal strengths of switches or the availability of new repeatable thoughts 9), or any combination thereof. The input command 18 and/or the function associated with the input command 18 can be, but need not be, irrelevant to the thought 9 associated with activating the input command 18. For example, FIGS. 1A-1C illustrate an exemplary variation of a non-specific, or universal, mode switching program (e.g., an application programming interface (API)) that third parties can plug into and which allows the thoughts 9 (e.g., the detectable neural-related signals and/or extractable features associated with the thoughts 9) to be assigned and reassigned to various input commands 18. By assigning the input command 18 a thought 9 is assigned to, or vice versa, the patient 8 can use the same thought 9 for various input commands 18 in the same or different end applications 12. Similarly, by reassigning the input command 18 a thought 9 is assigned to, or vice versa, the patient 8 can use the same thought 9 for various input commands 18 in the same or different end applications 12. For example, a thought 9 assigned to an input command 18 which causes a prosthetic hand (e.g., a first end application) to open can be assigned to a different input command 18 that causes a cursor (e.g., a second end application) to do something on a computer (e.g., any function associated with a cursor associated with a mouse or touchpad of a computer, including, for example, movement of the cursor and selection using the cursor such as left click and right click).

FIGS. 1A-1C further illustrate that the thoughts 9 of a patient 8 can be assigned to multiple end applications 12, such that the patient 8 can switch between multiple end applications 12 without having to reassign input commands 18 every time the patient 8 uses a different end application 12. For example, the thoughts 9 can be assigned to multiple end applications 12 simultaneously (e.g., to both a first end application and a second end application, where the process of assigning the thought 9 to both the first and second end applications can but need not occur simultaneously). A patient's thoughts 9 can thereby advantageously control any end application 12, including, for example, external gaming devices or various house appliances and devices (e.g., light switches, appliances, locks, thermostats, security systems, garage doors, windows, shades, including, any smart device or system, etc.). The neural interface 14 can thereby detect neural-related signals 17 (e.g., brain signals) that are task-irrelevant to the functions associated with the input commands 18 of the end applications 12, where the end applications 12 can be any electronic device or software, including devices internal and/or external to the patient's body. As another example, the neural interface 14 can thereby detect neural-related signals 17 (e.g., brain signals) that are task-relevant to the functions associated with the input commands 18 of the end applications 12, where the end applications 12 can be any electronic device or software, including devices internal and/or external to the patient's body. As yet another example, the neural interface 14 can thereby detect neural-related signals 17 (e.g., brain signals) associated with task-relevant thoughts, task-irrelevant thoughts, or both task-relevant thoughts and task-irrelevant thoughts.

Some of the thoughts 9 can be task-irrelevant thoughts (e.g., the patient 8 tries moving their hand to move a cursor to the right), some of the thoughts 9 can be task-relevant thoughts (e.g., the patient 8 tries moving a cursor when the target task is to move a cursor), some of the thoughts 9 can be both a task-irrelevant thought and a task-relevant thought, or any combination thereof. Where a thought 9 is both a task-irrelevant thought and a task-relevant thought, the thought 9 can be used as both a both a task-irrelevant thought (e.g., the patient 8 tries moving their hand to move a cursor to the right) and a task-relevant thought (e.g., the patient tries moving a cursor when the target task is to move a cursor) such that the thought 9 can be associated with multiple input commands 18, where one or multiple of those input commands 18 can be task-relevant to the thought 9 and where one or multiple of those input commands 18 can be task-irrelevant to the thought 9. As another example, all of the thoughts 9 can be task-irrelevant thoughts. The thoughts 9 that are task-irrelevant and/or the thoughts 9 used by the patient 8 as task-irrelevant thoughts (e.g., the thoughts 9 assigned to input commands 18 that are irrelevant to the thought 9) the patient 8 (e.g., BCI users) to utilize a given task-irrelevant thought (e.g., the thought 9) to independently control a variety of end-applications 12, including software and devices.

FIGS. 1A-1C illustrate, for example, that the patient 8 can think about the thought 9 (e.g., with or without being asked to think about the thought 9) and then rest. This task of thinking about the thought 9 can generate a detectable neural-related signal that corresponds to the thought 9 that the patient was thinking. The task of thinking about the thought 9 and then resting can be performed once, for example, when the patient 8 thinks of the thought 9 to control the end application 12. As another example, the task of thinking about the thought 9 can be repeated multiple times, for example, when the patient 8 is controlling an end application 12 by thinking of the thought 9 or when the patient is training how use the thought 9 to control an end application 12. When a neural-related signal (e.g., brain-related signal) is recorded, such as a neural signal, features can be extracted from (e.g., spectra power/time-frequency domain) or identified in the signal itself (e.g., time-domain signal). These features can contain characteristic information about the thought 9 and can be used to identify the thought 9, to distinguish multiple thoughts 9 from one another, or to do both. As another example, these features can be used to formulate or train a mathematical model or algorithm that can predict the type of thought that generated the neural-signal using machine learning methods and other methods. Using this algorithm and/or model, what the patient 8 is thinking can be predicted in real-time and this prediction can be associated into any input command 18 desired. The process of the patient 8 thinking about the same thought 9 can be repeated, for example, until the prediction provided by the algorithm and/or model matches the thought 9 of the patient 8. In this way, the patient 8 can have each of their thoughts 9 that they will use to control an end application 12 calibrated such that each thought 9 assigned to an input command 18 generates a repeatable neural-related signal detectable by the neural interface 14. The algorithm can provide feedback 19 to the patient 8 of whether the prediction matches the actual thought 9 that they are supposed to be thinking, where the feedback can be visual, auditory and/or tactile which can induce learning by the patient 8 through trial and error. Machine learning methods and mathematical algorithms can be used to classify the thoughts 9 based on the features extracted from and/or identified in the sensed neural-related signals 17. For example, a training data set can be recorded where the patient 8 rests and thinks multiple times, the processor can extract the relevant features from the sensed neural-related signals 17, and the parameters and hyperparameters of the mathematical model or algorithm being used to distinguish between rest and thinking based on this data can be optimized to predict the real-time signal. Then, the same mathematical model or algorithm that has been tuned to predict the real-time signal advantageously allows the module 10 to translate the thoughts 9 into real-time universal switches.

FIG. 1A further illustrates that that the neural interface 14 can monitor the biological medium (e.g., the brain), such as electrical signals from the tissue (e.g., neural tissue) being monitored. FIG. 1A further illustrates that the neural-related signals 17 can be brain-related signals. The brain-related signals can be, for example, electrical signals from any portion or portions of the patient's brain (e.g., motor cortex, sensory cortex). As another example, the brain-related signals can be any signal (e.g., electrical, biochemical) detectable in the skull, can be any feature or features extracted from a detected brain-related signal (e.g., via a computer processor), or both. As yet another example, the brain-related signals can be electrical signals, can be any signal (e.g., biochemical signal) caused by an electrical signal, can be any feature or features extracted from a detected brain-related signal (e.g., via a computer processor), or any combination thereof.

FIG. 1A further illustrates that the end applications 12 can be separate from but in wired or wireless communication with the module 10. As another example, the module 10 (e.g., the host device 16) can be permanently or removably attached to or attachable to an end application 12. For example, the host device 16 can be removably docked with an application 12 (e.g., a device having software that the module 10 can communicate with). The host device 16 can have a port engageable with the application 12, or vice versa. The port can be a charging port, a data port, or both. For example, where the host device is a smartphone, the port can be a lightening port. As yet another example, the host device 16 can have a tethered connection with the application 12, for example, with a cable. The cable can be a power cable, a data transfer cable, or both.

FIG. 1B further illustrates that when the patient 8 thinks of a thought 9, the neural-related signal 17 can be a brain-related signal corresponding to the thought 9. FIG. 1B further illustrates that the host device 16 can have a processor (e.g., microprocessor) that analyzes (e.g., detects, decodes, classifies, or any combination thereof) the neural-related signals 17 received from the neural interface 14, associates the neural-related signals 17 received from the neural interface 14 to their corresponding input command 18, associates features extracted from (e.g., spectra power/time-frequency domain) or identified in the neural-related signal 17 itself (e.g., time-domain signal) received from the neural interface 14 to their corresponding input command 18, saves the neural-related signals 17 received from the neural interface 14, saves the signal analysis (e.g., the features extracted from or identified in the neural-related signal 17), saves the association of the neural-related signal 17 to the input command 18, saves the association of the features extracted from or identified in the neural-related signal 17 to the input command 18, or any combination thereof.

FIG. 1B further illustrates that the host device 16 can have a memory. The data saved by the processor can be stored in the memory locally, can be stored on a server (e.g., on the cloud), or both. The thoughts 9 and the data resulting therefrom (e.g., the detected neural-related signals 17, the extracted features, or both) can function as a reference library. For example, once a thought 9 is calibrated, the neural-related signal 17 associated with the calibrated thought and/or its signature (also referred to as extracted) features can be saved. A thought 9 can be considered calibrated, for example, when the neural-related signal 17 and/or the features extracted therefrom have a repeatable signature or feature identifiable by the processor when the neural-related signal 17 is detected by the neural interface 14. The neural-related signals being monitored and detected in real-time can then be compared to this stored calibrated data in real-time. Whenever one of the detected signals 17 and/or its extracted features match a calibrated signal, the corresponding input command 18 associated with the calibrated signal can be sent to the corresponding end application 12. For example, FIGS. 1A and 1B illustrate that the patient 8 can be trained to use the module 10 by calibrating the neural-related signals 17 associated with their thoughts 9 and storing those calibrations in a reference library. The training can provide feedback 19 to the patient 8.

FIG. 1C further illustrates an exemplary user interface 20 of the host device 16. The user interface 20 can be a computer screen (e.g., a touchscreen, a non-touchscreen). FIG. 1C illustrates an exemplary display of the user interface 20, including selectable systems 13, selectable input commands 18, and selectable end applications 12. A system 13 can be a grouping of one or multiple end applications 12. Systems 13 can be added to and removed from the host device 16. End applications 12 can be added to and removed from the host device 16. End applications 12 can be added to and removed from the systems 13. Each system 13 can have a corresponding set of input commands 18 that can be assigned to a corresponding set of end applications 12. As another example, the user interface 20 can show the input commands 18 for each of the activated end applications 12 (e.g., the remote). As yet another example, the user interface 20 can show the input commands 18 for the activated end applications (e.g., the remote) and/or for the deactivated end applications 12 (e.g., the stim sleeve, phone, smart home device, wheelchair). This advantageously allows the module 10 to control any end application 12. The user interface 20 allows the thoughts 9 to be easily assigned to various input commands 18 of multiple end applications 12. The system groupings of end applications (e.g., system 1 and system 2) advantageously allow the patient 8 to organize the end applications 12 together using the user interface 20. Ready-made systems 13 can be uploaded to the module and/or the patient 8 can create their own systems 13. For example, a first system can have all the end applications 12 the patient 8 uses that are associated with mobility (e.g., wheelchair, wheelchair lift). As another example, a second system can have all the end applications 12 the patient 8 uses that are associated with prosthetic limbs. As yet another example, a third system can have all the end applications 12 the patient 8 uses that are associated with smart household appliances. As still yet another example, a fourth system can have all the end applications 12 the patient 8 uses that are associated with software or devices that the patient uses for their occupation. End applications 12 can be in one or multiple systems 13. For example, an end application 12 (e.g., wheelchair) can be in both system 1 and/or system 2. Such organizational efficiency can make it easy for the patient 8 to manage their end applications 12. The module 10 can have one or multiple systems 13, for example, 1 to 1000 or more systems 13, including every 1 system 13 increment within this range (e.g., 1 systems, 2 systems, 10 systems, 100 systems, 500 systems, 1000 systems, 1005 systems, 2000 systems). For example, FIG. 1C illustrates that the module 10 can have a first system 13a (e.g., system 1) and a second system 13b (e.g., system 2). Also, while FIG. 1C illustrates that end applications 12 can be grouped into various systems 13, where each system has one or multiple end applications 12, as another example, the user interface 20 may not group the end applications into systems 13.

FIG. 1C further illustrates that the host device 16 can be used to assign thoughts 9 to the input commands 18. For example, a thought 9, the neural-related signal 17 associated with the thought 9, the extracted features of the neural-related signal 17 associated with the thought 9, or any combination thereof can be assigned to an input command 18 of a system 13, for example, by selecting the input command 18 (e.g., the left arrow) and selecting from a drop down menu showing the thoughts 9 and/or data associated therewith (e.g., the neural-related signal 17 associated with the thought 9, the extracted features of the neural-related signal 17 associated with the thought 9, or both) that can be assigned to the input command 18 selected. FIG. 1C further illustrates that when an input command 18 is triggered by a thought 9 or data associated therewith, feedback (e.g., visual, auditory and/or haptic feedback) can be provided to the patient 8. FIG. 1C further illustrates that the one or multiple end applications 12 can be activated and deactivated in a system 13. Activated end applications 12 may be in a powered on, a powered off, or in a standby state. Activated end applications 12 can receive triggered input commands 18. Deactivated end applications 12 may be in a powered on, a powered off, or in a standby state. In one example, deactivated end applications 12 may not be controllable by the thoughts 9 of the patient 8 unless the end application 12 is activated. Activating an end application 12 using the user interface 20 can power on the end application 12. Deactivating an end application 12 using the user interface 20 can power off the deactivated end application 12 or otherwise delink the module 10 from the deactivated end application 12 so that the processor does not associate neural-related signals 17 with the thoughts 9 assigned to the deactivated end application 12. For example, FIG. 1C illustrates an exemplary system 1 having five end applications 12, where the five end applications include 5 devices (e.g., remote, stim sleeve, phone, smart home device, wheelchair), where one of them (e.g., the remote) is activated and the others are deactivated. Once "start" is selected (e.g., via icon 20a), the patient 8 can control the end applications 12 of the systems (e.g., system 1) that are activated (e.g., the remote) with the input commands 18 associated with the end applications 12 of system 1. FIG. 1C further illustrates that any changes made using the user interface 20 can be saved using the save icon 20b and that any changes made using the user interface 20 can be canceled using the cancel icon 20c. FIG. 1C further illustrates that the end applications 12 can be electronic devices.

FIGS. 1A-1C illustrate that the same specific set of thoughts 9 can be used to control multiple end applications 12 (e.g., multiple end devices), thereby making the module 10 a universal switch module. The module 10 advantageously allows the patient 8 (e.g., BCI users) to utilize a given task-irrelevant thought (e.g., the thought 9) to independently control a variety of end-applications 12, including, for example, multiple software and devices. The module 10 can acquire neural-related signals (e.g., via the neural interface 14), can decode the acquired neural-related signals (e.g., via the processor), can associate the acquired neural-related signals 17 and/or the features extracted from these signals with the corresponding input command 18 of one or multiple end applications 12 (e.g., via the processor), and can control multiple end applications 12 (e.g., via the module 10). Using the module 10, the thoughts 9 can advantageously be used to control multiple end applications 12. For example, the module 10 can be used to control multiple end applications 12, where a single end application 12 can be controlled at a time. As another example, the module 10 can be used to control multiple end applications simultaneously. Each thought 9 can be assigned to an input command 18 of multiple applications 12. In this way, the thoughts 9 can function as universal digital switches, where the module 10 can effectively reorganize the patient's motor cortex to represent digital switches, where each thought 9 can be a digital switch. These digital switches can be universal switches, usable by the patient 8 to control multiple end applications 12, as each switch is assignable (e.g., via the module 10) to any input command 18 of multiple end applications 12 (e.g., an input command of a first end application and an input command of a second end application). The module 10 can, via the processor, discern between different thoughts 9 (e.g., between different switches).

The module 10 can interface with, for example, 1 to 1000 or more end applications 12, including every 1 end application 12 increment within this range (e.g., 1 end application, 2 end applications, 10 end applications, 100 end applications, 500 end applications, 1000 end applications, 1005 end applications, 2000 end applications). For example, FIG. 1C illustrates that the first system 13a can have a first end application 12a (e.g., a remote), a second end application 12b (e.g., a stim sleeve), a third end application 12c (e.g., a phone), a fourth end application 12d (e.g., a smart home device), and a fifth end application 12e (e.g., a wheelchair).

Each end application can have, for example, 1 to 1000 or more input commands 18 that can be associated with the thoughts 9 of the patient 8, or as another example, 1 to 500 or more input commands 18 that can be associated with the thoughts 9 of the patient 8, or as yet another example, 1 to 100 or more input commands 18 that can be associated with the thoughts 9 of the patient 8, including every 1 input command 18 within these ranges (e.g., 1 input command, 2 input commands, 10 input commands, 100 input commands, 500 input commands, 1000 input commands, 1005 input commands, 2000 input commands), and including any sub-range within these ranges (e.g., 1 to 25 or less input commands 18, 1 to 100 or less input commands 18, 25 to 1000 or less input commands 18) such that any number of input commands 18 can be triggered by the patient's thoughts 9, where any number can be, for example, the number of input commands 18 that the thoughts 9 of the patient 8 are assigned to. For example, FIG. 1C illustrates an exemplary set of input commands 18 that are associated with the activated end application(s) 12 (e.g., the first end application 12a), including a first end application first input command 18a (e.g., left arrow), a first end application second input command 18b (e.g., right arrow), and a first end application third input command 18c (e.g., enter). As another example, FIG. 1C illustrates an exemplary set of input commands 18 that are associated with the deactivated end application(s) 12 (e.g., the second end application 12b), including a second end application first input command 18d (e.g., choose an output), where the second end application first input command 18d has not been selected yet, but can be any input command 18 of the second end application 12b. The first end application first input command 18a is also referred to as the first input command 18a of the first end application 12a. The first end application second input command 18b is also referred to as the second input command 18b of the first end application 12a. The first end application third input command 18c is also referred to as the third input command 18c of the first end application 12a. The second end application first input command 18d is also referred to as the first input command 18d of the second end application 12b.

When the patient 8 thinks of a thought 9, the module 10 (e.g., via the processor) can associate the neural-related signals 17 associated with the thought 9 and/or features extracted therefrom with the input commands 18 that the thought 9 is assigned to, and the input commands 18 associated with the thought 9 can be sent to their corresponding end applications 12 by the module 10 (e.g., via a processor, a controller, or a transceiver). For example, if the thought 9 is assigned to the first input command 18*a* of the first end application 18*a*, the first input command 18*a* of the first end application 12*a* can be sent to the first end application 12*a* when the patient 8 thinks of the thought 9, and if the thought 9 is assigned to the first input command 18*d* of the second end application 12*b*, the first input command 18*d* of the second end application 12*b* can be sent to the second end application 12*b* when the patient 8 thinks of the thought 9. A single thought (e.g., the thought 9) can thereby interface with, or be used to control, multiple end applications 12 (first and second end applications 12*a*, 12*b*). Any number of thoughts 9 can be used as switches. The number of thoughts 9 used as switches can correspond to, for example, the number of controls (e.g., input commands 18) needed or desired to control an end application 12. A thought 9 can be assignable to multiple end applications 12. For example, the neural-related signals 17 and/or the features extracted therefrom that are associated with a first thought can be assigned to the first end application first input command 18*a* and can be assigned to the second end application first input command 18*d*. As another example, the neural-related signals 17 and/or the features extracted therefrom that are associated with a second thought can be assigned to the first end application second input command 18*a* and can be assigned to a third end application first input command. The first thought can be different from the second thought. The multiple end applications 12 (e.g., the first and second end applications 12*a*, 12*b*) can be operated independently from one another. Where the module 10 is used to control a single end application (e.g., the first end application 12*a*), a first thought can be assignable to multiple input commands 18. For example, the first thought alone can activate a first input command, and the first thought together with the second thought can activate a second input command different from the first input command. The thoughts 9 can thereby function as a universal switch even where only a single end application 12 is being controlled by the module 10, as a single thought can be combinable with other thoughts to make additional switches. As another example, a single thought can be combinable with other thoughts to make additional universal switches that are assignable to any input command 18 where multiple end applications 12 are controllable by the module 10 via the thoughts 9.

FIGS. 2A-2D illustrate that the neural interface 14 can be a stent 101. The stent 101 can have struts 108 and sensors 131 (e.g., electrodes). The stent 101 can be collapsible and expandable.

FIGS. 2A-2D further illustrate that the stent 101 can implanted in the vascular of a person's brain, for example, a vessel traversing the person's superior sagittal sinus. FIG. 2A illustrates an exemplary module 10 and FIGS. 2B-2D illustrate three magnified views of the module 10 of FIG. 2A. The stent 101 can be implanted for example, via the jugular vein, into the superior sagittal sinus (SSS) overlying the primary motor cortex to passively record brain signals and/or stimulate tissue. The stent 101, via the sensors 131, can detect neural-related signals 17 that are associated with the thought 9, for example, so that people who are paralyzed due to neurological injury or disease, can communicate, improve mobility and potentially achieve independent through direct brain control of assistive technologies such as end applications 12. FIG. 2C illustrates that the communication conduit 24 (e.g., the stent lead) can extend from the stent 101, pass through a wall of the jugular, and tunnel under the skin to a subclavian pocket. In this way, the communication conduit 24 can facilitate communications between the stent 101 and the telemetry unit 22.

FIGS. 2A-2D further illustrate that the end application 12 can be a wheelchair.

Figure 3:
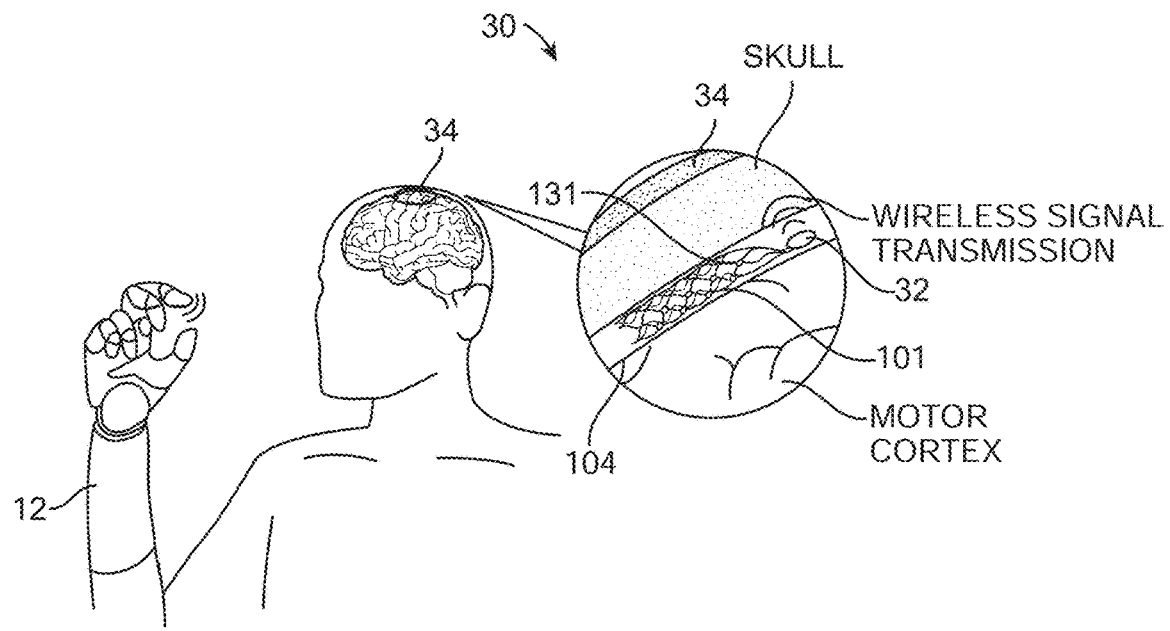
FIG. 3 illustrates a variation of a wireless universal switch module in communication with an end application.

FIG. 3 illustrates that the neural interface 14 (e.g., stent 101) can be a wireless sensor system 30 that can wirelessly communicate with the host device 16 (e.g., without the telemetry unit 22). FIG. 3 illustrates the stent 101 within a blood vessel 104 overlying the motor cortex in the patient 8 that are picking up neural-related signals and relaying this information to a wireless transmitter 32 located on the stent 101. The neural-related signals recorded by the stent 101 can be wirelessly transmitted through the patient's skull to a wireless transceiver 34 (e.g., placed on the head), which in turn, decodes and transmits the acquired neural-related signals to the host device 16. As another example, the wireless transceiver 34 can be part of the host device 16.

FIG. 3 further illustrates that the end application 12 can be a prosthetic arm.

Figure 4:
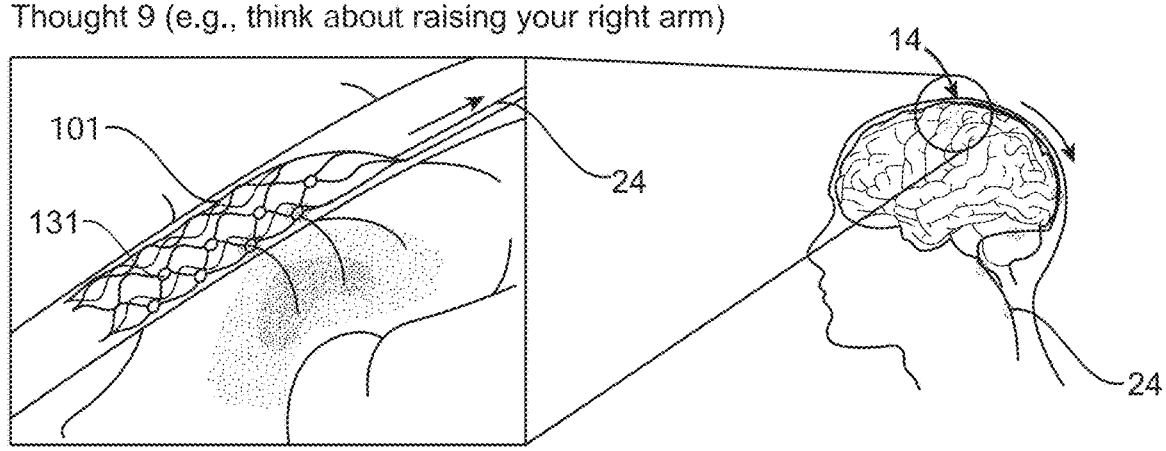
FIG. 4 illustrates a variation of a universal switch module being used to record neural-related signals of a patient.

FIG. 4 illustrates that the neural interface 14 (e.g., the stent 101) can be used to record neural-related signals 17 from the brain, for example, from neurons in the superior sagittal sinus (SSS) or branching cortical veins, including the steps of: (a) implanting the neural interface 14 in a vessel 104 in the brain (e.g., the superior sagittal sinus, the branching cortical veins); (b) recording neural-related signals; (c) generating data representing the recorded neural-related signals; and (d) transmitting the data to the host device 16 (e.g., with or without the telemetry unit 22).

Everything in U.S. patent application Ser. No. 16/054,657 filed Aug. 3, 2018 is herein incorporated by reference in its entirety for all purposes, including all systems, devices, and methods disclosed therein, and including any combination of features and operations disclosed therein. For example, the neural interface 14 (e.g., the stent 101) can be, for example, any of the stents (e.g., stents 101) disclosed in U.S. patent application Ser. No. 16/054,657 filed Aug. 3, 2018.

Using the module 10, the patient 8 can be prepared to interface with multiple end applications 12. Using the module 10, the patient 8 can perform multiple tasks with the use of one type of electronic command which is a function of a particular task-irrelevant thought (e.g., the thought 9). For example, using the module 10, the patient 8 can perform multiple tasks with a single task-irrelevant thought (e.g., the thought 9).

Figure 5:
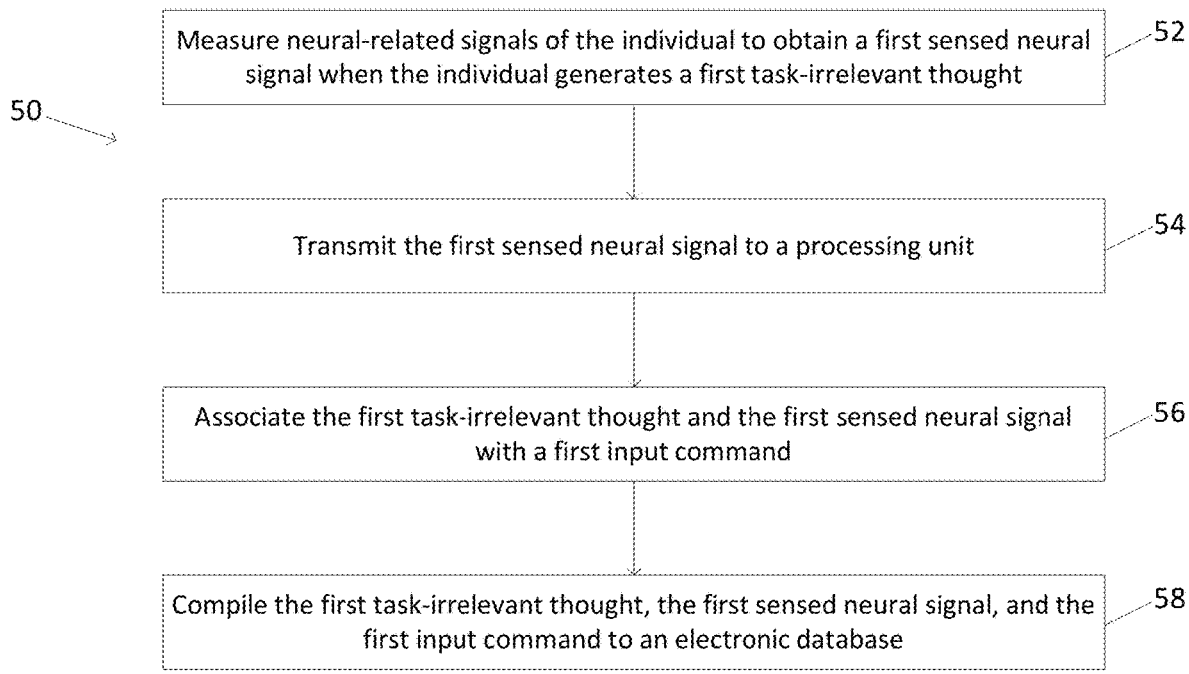
FIG. 5 illustrates a variation of a method undertaken by the universal switch module of FIGS. 1A-1C.

For example, FIG. 5 illustrates a variation of a method 50 of preparing an individual to interface with an electronic device or software (e.g., with end applications 12) having operations 52, 54, 56, and 58. FIG. 5 illustrates that the method 50 can involve measuring neural-related signals of the individual to obtain a first sensed neural signal when the individual generates a first task-irrelevant thought in operation 52. The method 50 can involve transmitting the first sensed neural signal to a processing unit in operation 54. The method 50 can involve associating the first task-irrelevant thought and the first sensed neural signal with a first input command in operation 56. The method 50 can involve compiling the first task-irrelevant thought, the first sensed neural signal, and the first input command to an electronic database in operation 58.

Figure 6:
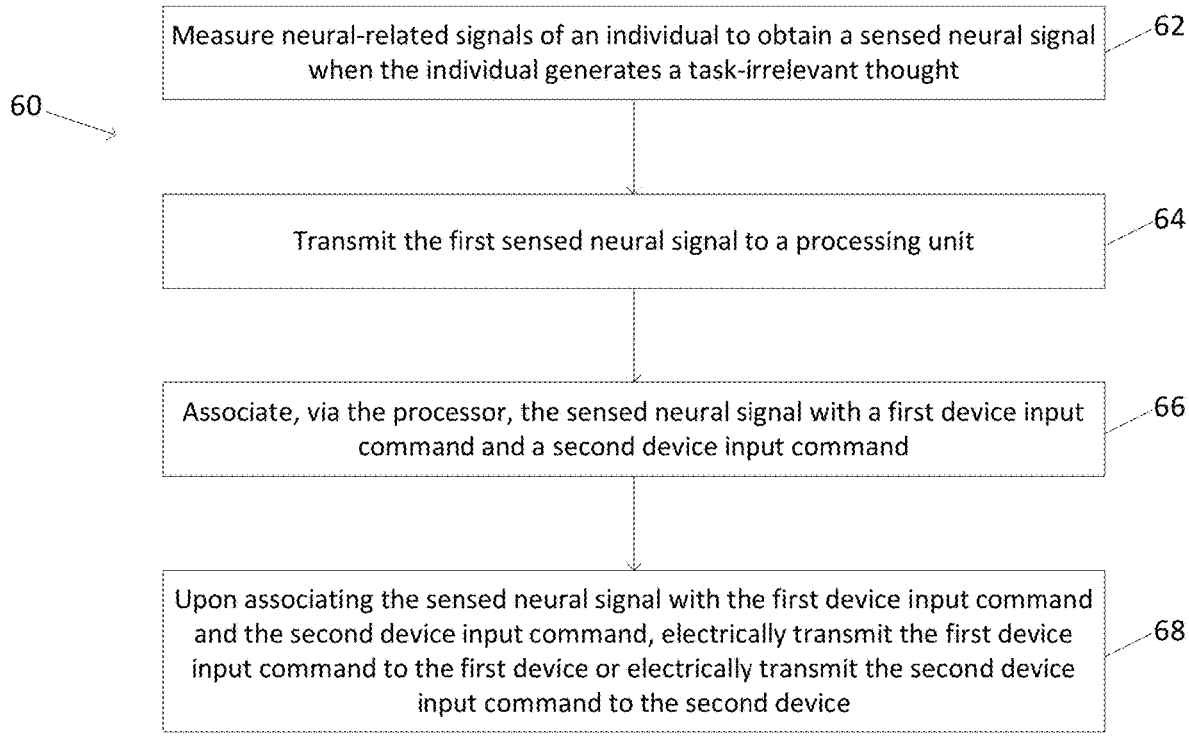
FIG. 6 illustrates a variation of a method undertaken by the universal switch module of FIGS. 1A-1C.

As another example, FIG. 6 illustrates a variation of a method 60 of controlling a first device and a second device (e.g., first and second end applications 12a, 12b) having operations 62, 64, 66, and 68. FIG. 6 illustrates that the method 60 can involve measuring neural-related signals of an individual to obtain a sensed neural signal when the individual generates a task-irrelevant thought in operation 62. The method 60 can involve transmitting the sensed neural signal to a processor in operation 64. The method can involve associating, via the processor, the sensed neural signal with a first device input command and a second device input command in operation 66. The method can involve upon associating the sensed neural signal with the first device input command and the second device input command, electrically transmitting the first device input command to the first device or electrically transmitting the second device input command to the second device in operation 68.

Figure 7:
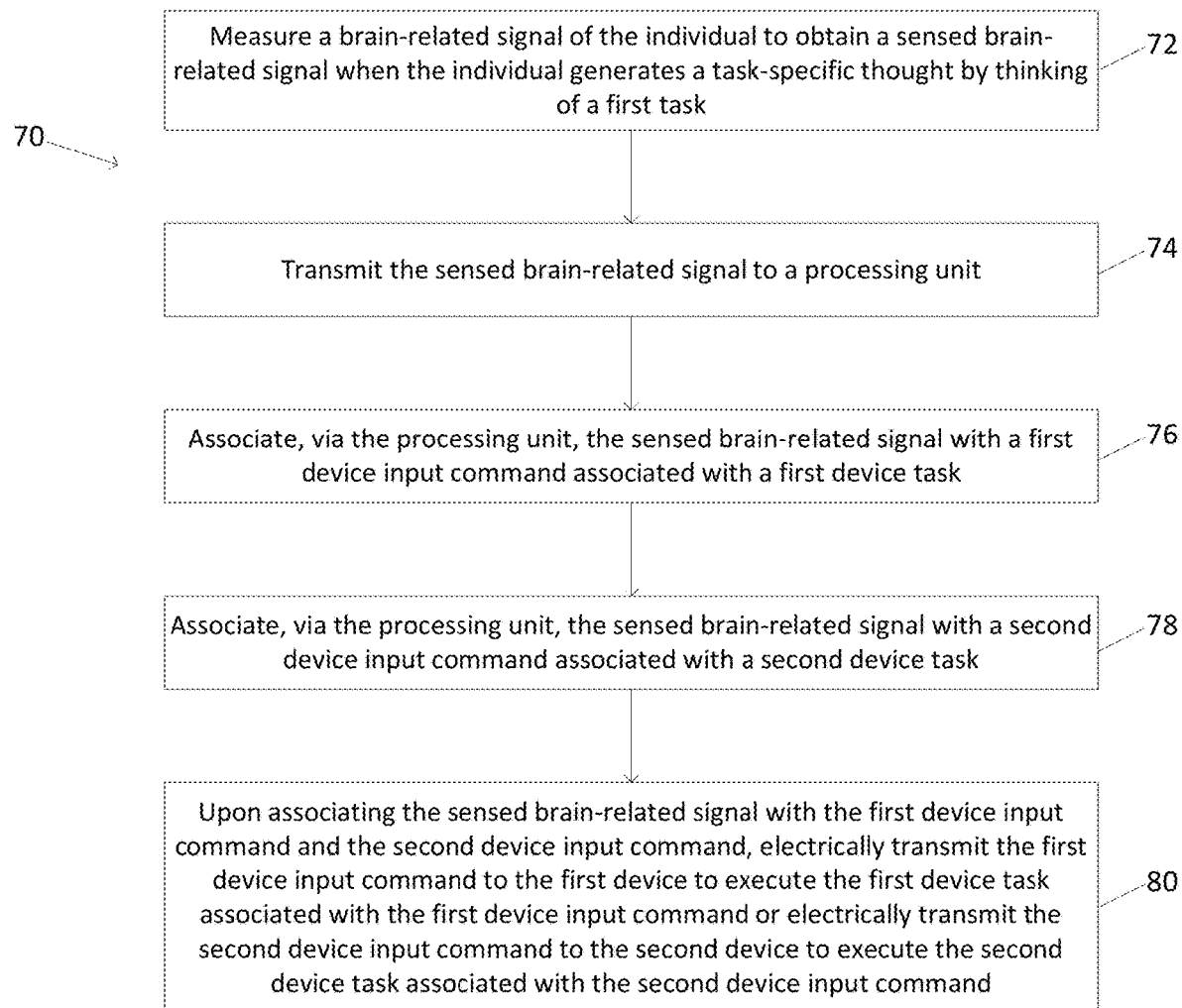
FIG. 7 illustrates a variation of a method undertaken by the universal switch module of FIGS. 1A-1C.

As another example, FIG. 7 illustrates a variation of a method 70 of preparing an individual to interface with a first device and a second device (e.g., first and second end applications 12a, 12b) having operations 72, 74, 76, 78, and 80. FIG. 7 illustrates that the method 70 can involve measuring a brain-related signal of the individual to obtain a sensed brain-related signal when the individual generates a task-specific thought by thinking of a first task in operation 72. The method can involve transmitting the sensed brain-related signal to a processing unit in operation 74. The method can involve associating, via the processing unit, the sensed brain-related signal with a first device input command associated with a first device task in operation 76. The first device task can be different from the first task. The method can involve associating, via the processing unit, the sensed brain-related signal with a second device input command associated with a second device task in operation 78. The second device task can be different from the first device task and the first task. The method can involve upon associating the sensed brain-related signal with the first device input command and the second device input command, electrically transmitting the first device input command to the first device to execute the first device task associated with the first device input command or electrically transmitting the second device input command to the second device to execute the second device task associated with the second device input command in operation 80.

As another example, FIGS. 5-7 illustrate variations of methods of controlling multiple end applications 12 with a universal switch (e.g., the thought 9).

As another example, the operations illustrated in FIGS. 5-7 can be executed and repeated in any order and in any combination. FIGS. 5-7 do not limit the present disclosure in any way to the methods illustrated or to the particular order of operations that are listed. For example, the operations listed in methods 50, 60, and 70 can be performed in any order or one or more operations can be omitted or added.

As another example, a variation of a method using the module 10 can include measuring brain-related signals of the individual to obtain a first sensed brain-related signal when the individual generates a task-irrelevant thought (e.g., the thought 9). The method can include transmitting the first sensed brain-related signal to a processing unit. The method can include the processing unit applying a mathematical algorithm or model to detect the brain-related signals corresponding to when the individual generates the thought 9. The method can include associating the task-irrelevant thought and the first sensed brain-related signal with one or multiple N input commands 18. The method can include compiling the task-irrelevant thought (e.g., the thought 9), the first sensed brain-related signal, and the N input commands 18 to an electronic database. The method can include monitoring the individual for the first sensed brain-related signal (e.g., using the neural interface), and upon detecting the first sensed brain-related signal electrically transmitting at least one of the N input commands 18 to a control system. The control system can be a control system of an end application 12. The N input commands 18 can be, for example, 1 to 100 input commands 18, including every 1 input command 18 within this range. The N input commands can be assignable to Y end applications 12, where the Y end applications can be, for example, 1 to 100 end applications 12, including every 1 end application 12 increment within this range. As another example, the Y end applications 12 can be, for example, 2 to 100 end applications 12, including every 1 end application 12 increment within this range. The Y end applications 12 can include, for example, at least one of controlling a mouse cursor, controlling a wheelchair, and controlling a speller. The N input commands 18 can be at least one of a binary input associated with the task-irrelevant thought, a graded input associated with the task-irrelevant thought, and a continuous trajectory input associated with the task-irrelevant thought. The method can include associating M detections of the first sensed brain-related signal with the N input commands 18, where M is 1 to 10 or less detections. For example, when M is one detection, the task-irrelevant thought (e.g., the thought 9) and the first sensed brain-related signal can be associated with a first input command (e.g., first input command 18a). As another example, when M is two detections, the task-irrelevant thought (e.g., the thought 9) and the first sensed brain-related signal can be associated with a second input command (e.g., first input command 18b). As yet another example, when M is three detections, the task-irrelevant thought (e.g., the thought 9) and the first sensed brain-related signal can be associated with a third input command (e.g., third input command 18c). The first, second, and third input commands can be associated with one or multiple end applications 12. For example, the first input command can be an input command for a first end application, the second input command can be an input command for a second end application, and the third input command can be an input command for a third application, such that a single thought 9 can control multiple end applications 12. Each number of M detections of the thought 9 can be assigned to multiple end applications, such that end number of M detections (e.g., 1, 2, or 3 detections) can function as a universal switch assignable to any input command 18. The first, second, and third input commands can be associated with different functions. The first, second, and third input commands can be associated with the same function such that the first input command is associated with a function first parameter, such that the second input command is associated with a function second parameter, and such that the third input command is associated with a function third parameter. The function first, second, and third parameters can be, for example, progressive levels of speed, volume, or both. The progressive levels of speed can be, for example, associated with movement of a wheelchair, with movement of a mouse cursor on a screen, or both. The progressive levels of volume can be, for example, associated with sound volume of a sound system of a car, a computer, a telephone, or any combination thereof. At least one of the N input commands 18 can be a click and hold command associated with a computer mouse. The method can include associating combinations of task-irrelevant thoughts (e.g., the thoughts 9)

with the N input commands 18. The method can include associating combinations of Z task-irrelevant thoughts with the N input commands 18, where the Z task-irrelevant thoughts can be 2 to 10 or more task-irrelevant thoughts, or more broadly, 1 to 1000 or more task-irrelevant thoughts, including every 1 unit increment within these ranges. At least one of the Z task-irrelevant thoughts can be the task-irrelevant thought, where the task-irrelevant thought can be a first task-irrelevant thought, such that the method can include measuring brain-related signals of the individual to obtain a second sensed brain-related signal when the individual generates a second task-irrelevant thought, transmitting the second sensed brain-related signal to a processing unit, associating the second task-irrelevant thought and the second sensed brain-related signal with N2 input commands, where when a combination of the first and second sensed brain-related signals are sequentially or simultaneously obtained, the combination can be associated with N3 input commands. The task-irrelevant thought can be the thought of moving a body limb. The first sensed brain-related signal can be at least one of an electrical activity of brain tissue and a functional activity of the brain tissue. Any operation in this exemplary method can be performed in any combination and in any order.

As another example, a variation of a method using the module 10 can include measuring a brain-related signal of the individual to obtain a first sensed brain-related signal when the individual generates a first task-specific thought by thinking of a first task (e.g., by thinking of the thought 9). The method can include transmitting the first sensed brain-related signal to a processing unit. The method can include the processing unit applying a mathematical algorithm or model to detect the brain-related signals corresponding to when the individual generates the thought. The method can include associating the first sensed brain-related signal with a first task-specific input command associated with a second task (e.g., an input command 18), where the second task is different from the first task (e.g., such that the thought 9 involves a different task than the task that the input command 18 is configured to execute). The first task-specific thought can be irrelevant to the associating step. The method can include assigning the second task to the first task-specific command instruction irrespective of the first task. The method can include reassigning a third task to the first task-specific command instruction irrespective of the first task and the second task. The method can include compiling the first task-specific thought, the first sensed brain-related signal, and the first task-specific input command to an electronic database. The method can include monitoring the individual for the first sensed brain-related signal, and upon detecting the first sensed brain-related signal electrically transmitting the first task-specific input command to a control system. The first task-specific thought can be, for example, about a physical task, a non-physical task, or both. The thought generated can be, for example, a single thought or a compound thought. The compound thought can be two or more non-simultaneous thoughts, two or more simultaneous thoughts, and/or a series of two or more simultaneous thoughts. Any operation in this exemplary method can be performed in any combination and in any order.

As another example, a variation of a method using the module 10 can include measuring a brain-related signal of the individual to obtain a first sensed brain-related signal when the individual thinks a first thought. The method can include transmitting the first sensed brain-related signal to a processing unit. The method can include the processing unit applying a mathematical algorithm or model to detect the brain-related signals corresponding to when the individual generates the thought. The method can include generating a first command signal based on the first sensed brain-related signal. The method can include assigning a first task to the first command signal irrespective of the first thought. The method can include disassociating the first thought from the first sensed electrical brain activity. The method can include reassigning a second task to the first command signal irrespective of the first thought and the first task. The method can include compiling the first thought, the first sensed brain-related signal, and the first command signal to an electronic database. The method can include monitoring the individual for the first sensed brain-related signal, and upon detecting the first sensed brain-related signal electrically transmitting the first input command to a control system. The first thought can involve, for example, a thought about a real or imagined muscle contraction, a real or imagined memory, or both, or any abstract thoughts. The first thought can be, for example, a single thought or a compound thought. Any operation in this exemplary method can be performed in any combination and in any order.

As another example, a variation of a method using the module 10 can include measuring electrical activity of brain tissue of the individual to obtain a first sensed electrical brain activity when the individual thinks a first thought. The method can include transmitting the first sensed electrical brain activity to a processing unit. The method can include the processing unit applying a mathematical algorithm or model to detect the brain-related signals corresponding to when the individual generates the thought. The method can include generating a first command signal based on the first sensed electrical brain activity. The method can include assigning a first task and a second task to the first command signal. The first task can be associated with a first device, and where the second task is associated with a second device. The first task can be associated with a first application of a first device, and where the second task is associated with a second application of the first device. The method can include assigning the first task to the first command signal irrespective of the first thought. The method can include assigning the second task to the first command signal irrespective of the first thought. The method can include compiling the first thought, the first sensed electrical brain activity, and the first command signal to an electronic database. The method can include monitoring the individual for the first sensed electrical brain activity, and upon detecting the first sensed electrical brain activity electrically transmitting the first command signal to a control system. Any operation in this exemplary method can be performed in any combination and in any order.

As another example, a variation of a method using the module 10 can include measuring neural-related signals of the individual to obtain a first sensed neural signal when the individual generates a task-irrelevant thought. The method can include transmitting the first sensed neural signal to a processing unit. The method can include the processing unit applying a mathematical algorithm or model to detect the brain-related signals corresponding to when the individual generates the task-irrelevant thought. The method can include associating the task-irrelevant thought and the first sensed neural signal with a first input command. The method can include compiling the task-irrelevant thought, the first sensed neural signal, and the first input command to an electronic database. The method can include monitoring the individual for the first sensed neural signal, and upon detecting the first sensed neural signal electrically transmitting the first input command to a control system. The neural-related signals can be brain-related signals. The neural-related signals can be measured from neural tissue in the individual's brain. Any operation in this exemplary method can be performed in any combination and in any order.

As another example, a variation of a method using the module 10 can include measuring a neural-related signal of the individual to obtain a first sensed neural-related signal when the individual generates a first task-specific thought by thinking of a first task. The method can include transmitting the first sensed neural-related signal to a processing unit. The method can include the processing unit applying a mathematical algorithm or model to detect the brain-related signals corresponding to when the individual generates the thought. The method can include associating the first sensed neural-related signal with a first task-specific input command associated with a second task, where the second task is different from the first task, thereby providing a mechanism to the user to control multiple tasks with different task-specific inputs with a single user-generated thought The method can include compiling the task-irrelevant thought, the first sensed neural signal, the first input command and the corresponding tasks to an electronic database. The method can include utilizing the memory of the electronic database to automatically group the combination of task-irrelevant thought, sensed brain-related signal and one or multiple N input based on the task, brain-related signal or the thought to automatically map the control functions for automatic system setup for use. The neural-related signal can be a neural-related signal of brain tissue. Any operation in this exemplary method can be performed in any combination and in any order.

The module 10 can perform any combination of any method and can perform any operation of any method disclosed herein.

The claims are not limited to the exemplary variations shown in the drawings, but instead may claim any feature disclosed or contemplated in the disclosure as a whole. Any elements described herein as singular can be pluralized (i.e., anything described as "one" can be more than one). Any species element of a genus element can have the characteristics or elements of any other species element of that genus. Some elements may be absent from individual figures for reasons of illustrative clarity. The above-described configurations, elements or complete assemblies and methods and their elements for carrying out the disclosure, and variations of aspects of the disclosure can be combined and modified with each other in any combination, and each combination is hereby explicitly disclosed. All devices, apparatuses, systems, and methods described herein can be used for medical (e.g., diagnostic, therapeutic or rehabilitative) or non-medical purposes. The words "may" and "can" are interchangeable (e.g., "may" can be replaced with "can" and "can" can be replaced with "may"). Any range disclosed can include any subrange of the range disclosed, for example, a range of 1-10 units can include 2-10 units, 8-10 units, or any other subrange. Any phrase involving an "A and/or B" construction can mean (1) A alone, (2) B alone, (3) A and B together, or any combination of (1), (2), and (3), for example, (1) and (2), (1) and (3), (2) and (3), and (1), (2), and (3). For example, the sentence "the module 10 (e.g., the host device 16) can be in wired and/or wireless communication with the one or multiple end applications 12" in this disclosure can include (1) the module 10 (e.g., the host device 16) can be in wired communication with the one or multiple end applications 12, (2) the module 10 (e.g., the host device 16) can be in wireless communication with the one or multiple end applications 12, (3) the module 10 (e.g., the host device 16) can be in wired and wireless communication with the one or multiple end applications 12, or any combination of (1), (2), and (3).

I claim:

1. A method of calibrating neural signals as electronic switches to permit an individual to control an electronic device, the method comprising:
    measuring neural-related signals when the individual generates a task-irrelevant thought associated with muscle contraction to obtain a sensed neural signal;
    transmitting the sensed neural signal to a processing unit;
    associating the first task-irrelevant thought and the sensed neural signal with a universal switch in the processing unit, where the universal switch is assigned to an input command of the electronic device in the processing unit, and where the universal switch is assigned to the input command of the electronic device via a user interface; and
    compiling the task-irrelevant thought, the sensed neural signal, and the input command to a database stored in electronic format which allows the individual to control the electronic device by producing the task-irrelevant thought to cause electrical transmission of the input command to the electronic device.

2. The method of claim 1, where the sensed neural signal is electrical brain activity.

3. The method of claim 1, where measuring neural-related signals comprises measuring neural-related signals of the individual with an implanted endovascular device.

4. A method of calibrating neural signals as electronic switches to permit an individual to independently and selectively control a first device and a second device, the method comprising:
    measuring neural-related signals when the individual generates a task-irrelevant thought associated with muscle contraction to obtain a sensed neural signal;
    transmitting the sensed neural signal to a processor;
    calibrating, via the processor, a universal switch based on the sensed neural signal, where the universal switch is assigned to an input command of the first device via the processor, where the universal switch is assigned to an input command of the second device via the processor, and where the universal switch is assigned to the input command of the first device and of the second device via a user interface; and
    compiling the task-irrelevant thought, the sensed neural signal, the input command of the first device, and the input command of the second device to a database stored in electronic format which allows the individual to control the first device or the second device by producing the task-irrelevant thought to cause electrical transmission of the input command of the first device to the first device or to cause electrical transmission of the input command of the second device to the second device.

5. The method of claim 4, where compiling the task-irrelevant thought, the sensed neural signal, the input command of the first device, and the input command of the second device to the database stored in electronic format allows the individual to control the first device and the second device by producing the task-irrelevant thought to cause electrical transmission of the input command of the first device to the first device and to cause electrical transmission of the input command of the second device to the second device.

6. The method of claim 4, where the sensed neural signal is sensed electrical brain activity.

7. The method of claim 4, where measuring neural-related signals comprises measuring neural-related signals of the individual with an implanted endovascular device.

8. The method of claim 4, where a function of the input command of the first device is unrelated to a function of the input command of the second device.

9. The method of claim 4, where the measuring, transmitting, and calibrating steps are performed independently of a device.

10. A method for preparing an individual to use their thoughts as universal electronic switches to control an electronic device, the method comprising:
calibrating a first universal switch by measuring neural-related signals of the individual to obtain a first sensed neural signal when the individual generates a first task-irrelevant thought, transmitting the first sensed neural signal to a processing unit, associating the first task-irrelevant thought and the first sensed neural signal with the first universal switch, and assigning the first universal switch to a first input command of the electronic device in the processing unit;
calibrating a second universal switch by measuring neural-related signals of the individual to obtain a second sensed neural signal when the individual generates a second task-irrelevant thought, transmitting the second sensed neural signal to the processing unit, associating the second task-irrelevant thought and the second sensed neural signal with the second universal switch, and assigning the second universal switch to a second input command of the electronic device in the processing unit;
associating a combination of the first task-irrelevant thought and the second task-irrelevant thought with a third universal switch; and
compiling the first task-irrelevant thought, the first sensed neural signal, the second task-irrelevant thought, and the second sensed neural signal to a database stored in electronic format which allows the individual to control the electronic device by producing the combination of the first task-irrelevant thought and the second task-irrelevant thought,
where, via a user interface, the first universal switch is assigned to the first input command of the electronic device and the second universal switch is assigned to the second input command of the electronic device.

11. The method of claim 10, where the first input command is any input command selectable from the user interface.

12. The method of claim 10, where the first task-irrelevant thought is a thought associated with muscle contraction.

13. The method of claim 10, where the second task-irrelevant thought is a thought associated with muscle contraction.

14. The method of claim 10, where the first and second task-irrelevant thoughts are thoughts associated with muscle contraction.

15. The method of claim 10, further comprising assigning the third universal switch to a third input command of the electronic device in the processing unit.

16. The method of claim 15, where compiling the first task-irrelevant thought, the first sensed neural signal, the second task-irrelevant thought, and the second sensed neural signal to the database stored in electronic format allows the individual to control the electronic device by producing the combination of the first task-irrelevant thought and the second task-irrelevant thought to cause electrical transmission of the third input command to the electronic device.

17. The method of claim 10, where compiling the first task-irrelevant thought, the first sensed neural signal, the second task-irrelevant thought, and the second sensed neural signal to the database stored in electronic format allows the individual to control the electronic device by producing the combination of the first task-irrelevant thought and the second task-irrelevant thought to cause electrical transmission of a third input command to the electronic device.

* * * * *